United States Patent [19]

Pinchuk

[11] Patent Number: 5,755,774
[45] Date of Patent: May 26, 1998

[54] BISTABLE LUMINAL GRAFT ENDOPROSTHESIS

[75] Inventor: Leonard Pinchuk, Miami, Fla.

[73] Assignee: Corvita Corporation, Miami, Fla.

[21] Appl. No.: 701,557

[22] Filed: Aug. 22, 1996

Related U.S. Application Data

[63] Continuation of Ser. No. 267,121, Jun. 27, 1994, abandoned.

[51] Int. Cl.$^6$ ............................................. A61F 2/06
[52] U.S. Cl. ............................................. 623/1
[58] Field of Search ............................................. 623/1

[56] References Cited

U.S. PATENT DOCUMENTS

| | | |
|---|---|---|
| 4,173,689 | 11/1979 | Lyman et al. |
| 4,323,525 | 4/1982 | Bornat . |
| 4,459,252 | 7/1984 | MacGregor . |
| 4,475,972 | 10/1984 | Wong . |
| 4,503,569 | 3/1985 | Dotter . |
| 4,512,338 | 4/1985 | Balke . |
| 4,580,568 | 4/1986 | Gianturco . |
| 4,655,771 | 4/1987 | Wallsten . |
| 4,712,553 | 12/1987 | MacGregor . |
| 4,733,665 | 3/1988 | Palmaz . |
| 4,738,740 | 4/1988 | Pinchuk et al. |
| 4,739,762 | 4/1988 | Palmaz . |
| 4,776,337 | 10/1988 | Palmaz . |
| 4,800,882 | 1/1989 | Gianturco ............... 128/343 |
| 4,873,308 | 10/1989 | Coury et al. |
| 4,950,227 | 8/1990 | Savin et al. ............... 623/1 |
| 4,994,071 | 2/1991 | MacGregor . |
| 4,995,872 | 2/1991 | Ferrara . |
| 5,019,090 | 5/1991 | Pinchuk . |
| 5,092,877 | 3/1992 | Pinchuk ............... 623/1 |
| 5,122,154 | 6/1992 | Rhodes . |
| 5,133,742 | 7/1992 | Pinchuk ............... 623/1 |
| 5,139,480 | 8/1992 | Hickle et al. |
| 5,156,620 | 10/1992 | Pigott . |
| 5,171,262 | 12/1992 | MacGregor . |
| 5,195,984 | 3/1993 | Schatz . |
| 5,282,823 | 2/1994 | Schwartz et al. ............... 623/1 |
| 5,443,499 | 8/1995 | Schmitt ............... 623/1 |

FOREIGN PATENT DOCUMENTS

| | | |
|---|---|---|
| 0009941 | 4/1980 | European Pat. Off. |
| 197787 | 10/1986 | European Pat. Off. |
| 341988 | 11/1989 | European Pat. Off. |
| 0461791 | 12/1991 | European Pat. Off. |
| 556850 | 8/1993 | European Pat. Off. |
| 3918736 | 12/1990 | Germany . |
| 1205743 | 9/1970 | United Kingdom . |
| 2115776 | 9/1983 | United Kingdom . |
| 9206734 | 4/1992 | WIPO . |

OTHER PUBLICATIONS

A. Balko et al., "Transfemoral Placement of Intraluminal Polyurethane Prostheses for Abdominal Aortic Aneurysm", Journal of Surgical Research, 40, 305–309, 1986.

*Primary Examiner*—Veronica P. Hoke
*Attorney, Agent, or Firm*—Lockwood, Alex, Fitzgibbon & Cummings

[57] ABSTRACT

A luminal graft endoprosthesis or endovascular graft is described which is capable of dilation and support functions and as suitable for the endoluminal repair of vascular lesions and the like. An expandable support or stent is combined with a tubular graft made of a material having two unstressed conditions to provide a combined stent-graft wherein the graft material is secured to either or both of the internal and external surfaces of the stent. The stent-graft may be positioned within a blood vessel of a living patient by an expandable balloon catheter. The graft member is made from a biocompatible material which, when expanded, exceeds its yield point and becomes dimensionally stable without retaining significant residual forces which may cause the stent to collapse after its placement within a blood vessel.

15 Claims, 2 Drawing Sheets

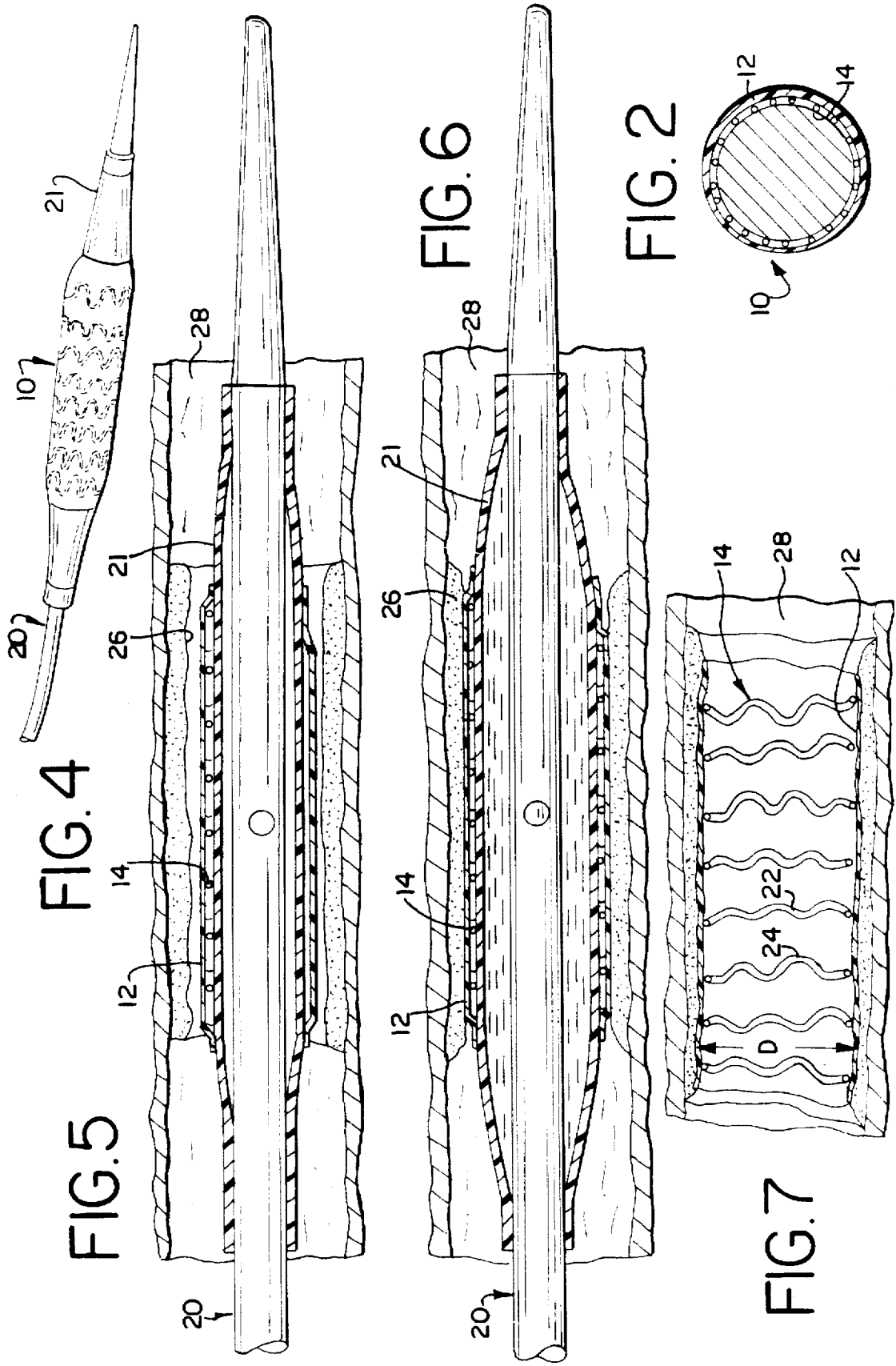

BISTABLE LUMINAL GRAFT ENDOPROSTHESIS

This application is a continuation, of application Ser. No. 08/267,121, filed Jun. 27, 1994, now abandoned.

BACKGROUND OF THE INVENTION

The present invention relates to luminal graft endoprostheses or endovascular grafts capable of dilation and support functions and suitable for the endoluminal repair of vascular lesions and the like. An expandable endovascular support or stent is combined with a graft made of a so-called bistable material to provide a combined stent-graft wherein the graft material is secured to either or both of the internal and external surfaces of the stent. The graft may be woven, non-woven, knitted or sheet material which is stretched beyond its yield point when the stent-graft is radially expanded.

Luminal endoprostheses having expandable coatings on the surface of external walls of radially expandable tubular supports or stents have been proposed and are known in the art. For example, U.S. Pat. Nos. 4,739,762 and 4,776,337 describe luminal endoprostheses with expandable coatings made from thin elastic polyurethane, teflon film, or a film of another inert biocompatible material. The film may have radially projecting ribs for fixation, and macroscopic openings to allow blood to flow between the covering and the lumen of the vessel in which the endoprosthesis is anchored. Other literature describes a coating from an elastomeric polyurethane film applied around a metallic support with form memory properties. See, A. Balko et al., "Transfemoral Placement of Intraluminal Polyurethane Prostheses for Abdominal Aortic Aneurysm", *Journal of Surgical Research*, 40, 305–309, 1986. In U.S. Pat. Nos. 5,019,090 and 5,092,877, the possibility of covering the support of a radially expandable endoprosthesis is generally mentioned but not described. These Approaches have often been unsatisfactory because the film materials used in these devices have not been sufficiently biocompatible.

Other supports or stents are known in which the support or stent is expanded by applying an exterior force from an inflating balloon, for example. U.S. Pat. Nos. 4,733,665; 4,739,762; 4,776,337; 4,800,882 and 5,019,090, for example, all describe such supports or stents. These patents are incorporated by reference hereinto. Other approaches include semi-rigid prostheses introduced endoluminally. These prosthesis typically are tubes which are connected to vessels to be reinforced by end supports.

The use of stents is known to lead to the unorganized development of cells within the mesh of the support or stent, resulting in the rapid reformation of the cellular thickening in the vessels to be protected, i.e. fibrous hyperplasia. Problems have also been noted in the use of tubular grafts, without a supporting stent, as endoprostheses because such unsupported grafts often lack a necessary degree of rigidity. Tubular supports also frequently fail to provide porous surfaces which promote cellular growth on the wall of the support. Following implantation, these devices continue to represent a foreign body within the human or animal patient. Because of the films used, normal and desirable cellular invasion into the prosthesis is not possible, especially along the inside of their structure.

Tube-formed, prostheses made from fibrous materials and having a structure of superimposed layers of fibers are known where the fibers of one layer intersect those of neighboring layers. These prostheses are used to replace fragments of defective vessels and are typically made of approximately 400 layers of interlaced fibers. In view of their proposed use to replace vessel fragments, these prostheses are not typically constructed to allow for their radial expansion. For example, Dacron or Teflon grafts have been proposed for stent-graft construction, but they must be folded axially because they are not stretchable. Such folded grafts have relatively large minimum diameters which present a rather bulky stent-graft when unexpanded that is not suitable for passage through many body passageways.

Additionally, luminal graft endoprostheses incorporating an expandable graft member and a structural support or stent member have been proposed wherein the stent-graft or endoprosthesis is introduced into the body in a collapsed configuration having a first diameter and is then expanded to an opened position having a second or expanded diameter. The graft member is typically made of an elastomeric material which, when stretched, retains stored energy which exerts forces against the stent or support member and which may, in turn, collapse the stent following implantation. To compensate for the force exerted by the expanded elastomeric graft, the stent or support member usually must have large hoop stresses. Supplying stents with such large hoop stresses typically implies a thick-walled stent, the use of which is impractical for vascular applications, especially in small diameter arteries where large lumens and thin walled prostheses are required. Also, stretching of the graft materials could contribute to degradation of the graft upon implantation for long periods of time under stretched or stressed conditions.

The art has generally failed to provide a luminal graft endoprosthesis which overcomes the aforementioned shortcomings of the prior art. It is, therefore, desirable to provide a luminal graft endoprosthesis which is sufficiently biocompatible and which possesses the combined advantages of stents and grafts while avoiding the aforementioned shortcomings. It is especially desirable to provide such a stent-graft having an expandable graft member capable of two stable configurations; a first or collapsed configuration having a first cross-sectional diameter and a second or expanded configuration having a larger cross-sectional diameter wherein the graft member is made of a biocompatible material which, when expanded, is stretched beyond its yield point and is thus dimensionally stable and does not retain significant residual stresses which may cause the stent to collapse. Graft members having these characteristics are referred to herein as "bistable" grafts.

BRIEF DESCRIPTION OF THE INVENTION

The present invention overcomes the shortcomings of the art by providing novel luminal graft endoprostheses for the endoluminal repair of vascular lesions and the like. The luminal graft endoprostheses or stent-grafts of the invention include a graft component capable of assuming two stable configurations and a stent component which provides structural support. The graft component is placed over the external and/or internal surface of the stent component and the stent-graft can be inserted within a vein or artery or other body pathway by placing it on a balloon catheter or similar device. The stent-graft is originally in an unexpanded state having a first cross-sectional diameter ("d") and is capable of being expanded to a second stable configuration with a second expanded cross-sectional diameter ("D").

The graft member is made of a material having yield point properties as discussed herein and can be woven, non-woven or knitted. The graft member is combined with the stent member, the stent-graft can be placed on a balloon catheter for insertion into a body pathway such as a blood vessel, for example. The stent-graft is expanded by the radial pressure exerted by the inflated balloon to an opened or expanded condition wherein the graft member is stretched beyond its yield point to reach a dimensionally stable state. The radial pressure exerted by the balloon to expand the graft member elongates the fibers of the graft to their yield point and, the graft will remain dimensionally stable beyond that yield point. For some materials, this can be considered to achieve orientation. The preferred material for the graft member, once expanded, retains no significant residual stresses in the yielded material which would tend to collapse the extended stent. Alternatively, the graft member may be made of a tubular film, preferably a porous film, of material having bistable properties which can be placed over the stent to form the stent-graft of the invention. Where film materials are used, it may be possible to first stretch the film in the axial direction so that when the stent-graft is radially expanded the graft member will have the properties of material stretched in two distinct directions. For some materials, this can be considered to achieve biaxial orientation.

The stent member of the stent-graft of the present invention can be selected from any known stent. The preferred stents are those which are balloon inflatable such as those described in U.S. Pat. No. 5,019,090 and U.S. Pat. No. 5,092,877 to Pinchuk, the disclosures of which are incorporated by reference herein.

It is, therefore, a general object of the present invention to provide an improved stent-graft that is expandable in place, and once expanded, is self-supporting.

Another object of the invention is to provide biocompatible grafts that are expandable in vivo and are supportive once so expanded.

Another object of the present invention is to provide an improved expandable reinforced graft that can be delivered by way of a balloon catheter or similar device.

Another object of the invention is to provide an improved endoluminal graft which covers diseased or damaged areas and is useful in carrying out luminal repairs or treatments.

Another object of the present invention is to provide a luminal graft endoprosthesis which includes a graft member and a stent member wherein the graft member is dimensionally stable in an unexpanded state as well as in an expanded state and, when in the expanded state, retains no significant residual stresses which could collapse the expanded stent member.

These and other objects, features and advantages of the invention will be more clearly understood by those skilled in the art following a detailed consideration of the remainder of the disclosure.

BRIEF DESCRIPTION OF THE DRAWINGS

In describing the preferred embodiment of the invention, reference will be made to the various drawings in which:

FIG. 2 is a cross-section of the stent-graft of FIG. 1 taken along the 2—2 line thereof;

FIG. 4 is a perspective view of an expandable stent-graft positioned on a balloon catheter according to the invention;

FIG. 5 is a side elevational view, in cross-section, of a stent-graft positioned in an unexpanded condition over a balloon catheter and within a blood vessel according to the invention;

FIG. 6 is a side elevational view showing the stent-graft and the balloon catheter of FIG. 5 in an expanded condition within the aforementioned blood vessel; and FIG. 7 is a side elevational view, in cross-section, of the stent-graft of the present invention positioned within a blood vessel.

DETAILED DESCRIPTION OF THE PREFERRED EMBODIMENT

Figure 1:
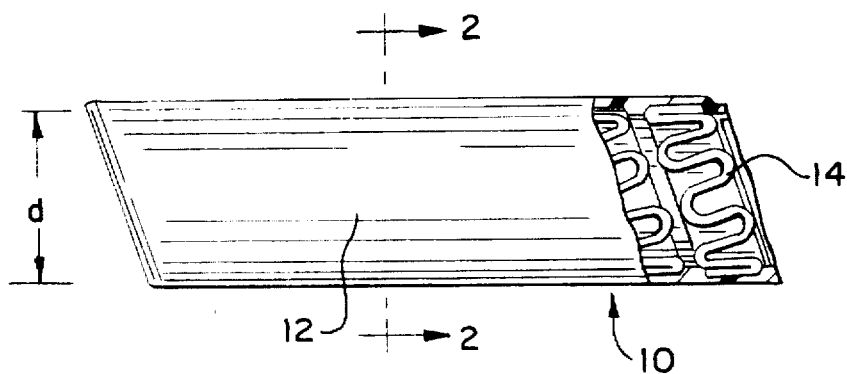
FIG. 1 is a side elevation, partially cut away, view of a stent-graft according to the invention.

The invention provides a stent-graft for the endoluminal repair of vascular lesions and the like. The stent-graft includes a graft member made of a bistable material which is secured to an expandable support component or stent to provide a combined stent-graft which can be inserted within a blood vessel or other body pathway on a balloon catheter or like device for the repair of a vascular lesion and the like. In referring to the preferred embodiment of the invention, reference is made to the various figures wherein the structural elements of the invention are indicated with reference numerals and wherein identical reference numerals indicate identical structures.

Referring now to the figures, FIGS. 1 and 2 illustrate a stent-graft 10 according to the present invention. The stent-graft 10 is essentially a two component expandable and supportive endoluminal graft. The first or graft component 12 overlays the second supportive or stent component 14. Those skilled in the art will understand, however, that the invention is not to be limited by the relative positioning or axial length of the aforementioned components 12 and 14. For example, the graft component 12 can substantially or partially cover the external surface or the internal surface of the stent component 14, as mentioned, or the graft can substantially or partially cover both the internal and external surfaces of the support component 14. The stent-graft 10 is constructed to be capable of two stable configurations, a first or unexpanded configuration having a first cross-sectional diameter ("d") and a second or expanded configuration wherein the stent-graft assumes a larger cross-sectional diameter ("D"). The stent-graft 10 and, more specifically, the graft component 12 is made of materials which exceed their yield point in the expanded configuration and which retain no significant residual stresses or forces within the material of the graft member 12 which could worn toward collapsing the stent-graft 10.

Figure 3:
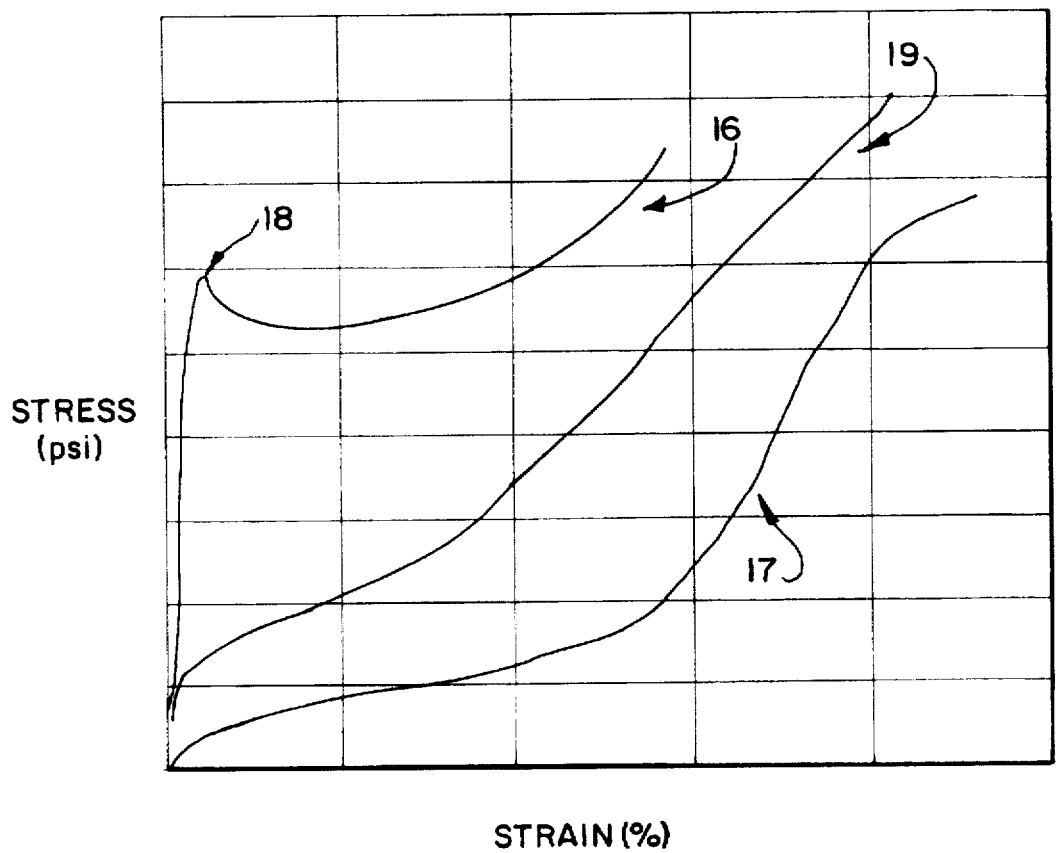
FIG. 3 is a representative stress-strain curve for materials suitable for use in the manufacture of the graft component of the stent-graft of the present invention as well as stress-strain curves of other materials also being shown.

The graft member 12 is made of an orientable material, as mentioned, and can be woven, non-woven, knitted or supplied in a single sheet of material. Suitable materials for the manufacture of the graft component 12 include without limitation polyester terephthalates such as polyethylene terephthalate (PET), polytetrafluoroethylene (PTFE), polyamide, polyurethane, polycarbonate polyurethane, poly (methylpentane), polypropylene, polyethylene, polyvinyl chloride (PVC) and other materials known to those skilled in the art and which are capable of exhibiting the bistable properties discussed herein.

Where polyurethanes are employed, consideration must be given to the nature of the polyurethane being employed so that only those with suitable yield points are used. For example, polycarbonate polyurethanes known under the trademark CORETHANE® 75D, available from Corvita Corporation are satisfactory. FIG. 3 illustrates a representative stress-strain curve for materials suited for use in the present invention. The curve 16 is typical of the aforementioned CORETHANE® 75D polyurethanes having a yield point 18 corresponding approximately to the inflation pressure of the balloon 20 (FIGS. 4–6). FIG. 3 illustrates stress-strain curves for other polyurethane materials which do not have this characteristic yield point property. Curve 19 is that of a polyurethane having a 55D Durometer hardness, and curve 17 is a stress-strain curve of a polyurethane having an 80A Durometer hardness.

As illustrated in FIG. 3, the material used in the graft will maintain structural integrity beyond the yield point 18. Preferably, the materials used in the graft component 12 should generally be capable of being radially expanded to a cross-sectional diameter two to six times that of the unexpanded state without weakening the material. Most typically, the material needs to be capable of maintaining a stable state when expanded four times its unexpanded state. Additionally, the graft component 12 should be free from significant residual elastic forces which could cause the stent member to contract. By choosing the appropriate bistable material for the graft component 12, the stent component 14 can be selected to allow the use of thin-walled stents. The absence of significant residual forces exerted by the graft 12 eliminates the need to have large hoop stresses in the stent 14. Consequently, the stent-grafts 10 of the present invention can be made for use in small diameter arteries where large lumens and thin walled prostheses are required.

The stent member 14 used in the stent-graft 10 of the present invention can be selected from any of a variety of stents known to those skilled in the art. The particular stent 14 depicted in phantom in FIG. 4, for example, is similar to, that disclosed in the aforementioned U.S. Pat. No. 5,019,090. The stent member 14 includes a plurality of generally circumferential sections, such as sections 22 and 24, for example. The sections of the stent member 14 are generally adjacent one another along their respective opposing circumferential edges. The stent member 14 of the stent-graft 10 includes at least one circumferential section having an expandable segment that imparts radial expandability to the circumferential section. Each expandable segment in the stent 14 is bendable between a generally collapsed or closed orientation (FIG. 5) and a generally opened orientation (FIGS. 6 and 7). Other structures for the stent member 14 are available and are known to those skilled in the art.

Regarding the construction of the stent-graft 10, the graft member can be manufactured by a spinning technique such that described in U.S. Pat. No. 4,475,972 the disclosure of which is incorporated by reference herein. Briefly, polymer in solution is extruded into fibers from the spinnerete onto a rotating mandrel. The spinnerete system is reciprocated along the longitudinal axis of the mandrel at a controlled pitch angle, resulting in a non-woven structure where each fiber layer is bound to the underlying layer. The stent member 14 can be placed directly on the mandrel and the layer of polymer fibers forming the graft member 12 can then be spun thereover. Alternatively, the layer of fibers can be spun directly onto the mandrel and, the stent member 14 is then applied over the mandrel with an additional layer of fibers then spun over the stent member 14 so that the stent member is coated on both its inner and outer surfaces.

The invention, however, is not limited to the above method of manufacturing the graft member 12. In addition to the above-described nonwoven graft, the graft member 12 can be a woven or knitted material, a polymeric film or the like having the bistable properties discussed herein. It is also possible to initially stretch the strands to beyond the yield point of the polymer and then form them into woven, knitted or non-woven grafts. The stent-graft formed with this material is then heat collapsed to its state below its yield point (such as a non-oriented state) and placed on a balloon catheter for implantation into a human or animal body pathway such as a blood vessel, for example.

Graft member 12 can be bonded to the stent member 14 by thermobonding and/or by the use of adhesive agents such as an adhesive, a hot melt adhesive, a silicone adhesive, a primer, a coupling agent, combinations thereof and the like. Both the graft 12 and the stent 14 are manufactured to be capable of expansion from a first cross-sectional diameter "d" to a second expanded cross-sectional diameter "D" by the application of a radially expansive force from within the stent-graft 10. Both the graft member 12 and the stent member 14 are constructed to be dimensionally stable when positioned in either the unexpanded or expanded states.

FIGS. 4 through 7 generally show the use of the stent-graft 10 in the treatment of endovascular lesions. A stenosis or lesion 26 within blood vessel 28 is transluminally reached by a balloon catheter 20 having a stent-graft 10 in its first or unexpanded stable condition overlying the collapsed balloon 21 of the catheter 20. The balloon 21 is expanded in a known manner, at which time the stent-graft 10 is also expanded by the radial force exerted by the balloon 21. FIG. 6 illustrates the balloon 21 and the stent-graft 10 in an intermediate dilation position with the lesion 26 initially dilated. FIG. 7 shows full dilation of the lesion 26 following the withdrawal of the balloon catheter 20. The bistable stent-graft 10 has attained its second or expanded stable condition and remains in place within the blood vessel 28 because of the hoop stress exerted by the stent-member 14 once expanded, as illustrated in FIG. 7. The stent member 14 must exert sufficient hoop stress to successfully resist inwardly directed radial forces presented by both the treated lesion 26 as well as the graft member 14. When fully expanded, the stent-graft 10 of the present invention assumes an expanded diameter "D" (FIG. 7) which Is typically two to six times that of the collapsed or unexpanded diameter "d" indicated in FIG. 2. The more typical expansion of the stent-graft 10 is on the order of four times the collapsed diameter "d".

While a preferred embodiment of the present invention has been described in detail herein, those skilled in the art will appreciate that various changes and modifications can be made to the described embodiment without departing from the true spirit and scope of the present invention, as defined in the following claims.

I claim:

1. A bistable luminal graft endoprosthesis, comprising:
a stent member having a generally cylindrical external surface and a generally cylindrical internal surface, said stent member being expandable from a first diameter at which it can be inserted into a human or animal body pathway and a second diameter greater than said first diameter; and
a polymeric material tubular graft member that engages at least one of said generally cylindrical external and internal surfaces of said stent member, said graft member has a collapsed stable configuration when said stent member is at said first diameter and assumes an expanded stable configuration when said stent member is at said second expanded diameter,
said graft member polymeric material having been pre-stretched to surpass the elastic yield point of the polymeric material, and said collapsed stable configuration of the graft member being one at which the graft member, during manufacture, had been collapsed over at least one of said generally cylindrical surfaces of the stent member to provide said collapsed stable configuration after the graft member polymeric material had been prestretched to surpass the elastic yield point;

said expanded stable configuration of the graft member being one at which the graft member, during use, expands to said second diameter after having been prestretched to surpass said elastic yield point;

said polymeric material is substantially unstressed when at both said collapsed and expanded stable configurations; and said polymer material is selected from the group consisting of polyester terephthalate, polytetrafluoroethylene, polyamide, poly(methylpentane), polypropylene, polyethylene, polyvinylchloride, polycarbonate polyurethane which has a Durometer hardness of 75D or harder, and combinations thereof.

2. The bistable luminal graft endoprosthesis as defined in claim 1 wherein said tubular graft member is made of woven, non-woven, knitted or film materials.

3. The bistable luminal graft endoprosthesis as defined in claim 1 wherein said graft member and said stent member are capable of being expanded from said collapsed diameter to said stretched diameter by the application of radially directed pressure from within said stent member, said graft member being constructed to surpass said elastic yield point without substantial weakening of said graft member when expanded to said second diameter.

4. The bistable luminal graft endoprosthesis as defined in claim 1 wherein said graft member and said stent member are dimensioned for placement over a balloon of a catheter for insertion into a living body pathway.

5. The bistable luminal graft endoprosthesis as defined in claim 1, wherein said tubular graft member is secured to at least one of said generally cylindrical external and internal surfaces of said stent member, and said graft member is made of an orientable polymeric material.

6. The bistable luminal graft endoprosthesis of claim 5 wherein said stent member and said tubular graft member are dimensioned to be placed on a balloon of a catheter for insertion into a human or animal body pathway.

7. The bistable luminal graft endoprosthesis of claim 5 wherein said stent member includes a plurality of generally circumferential adjacent sections wherein each said section includes at least one expandable segment which imparts radial expandability to said circumferential section.

8. The bistable luminal graft endoprosthesis as defined in claim 1 wherein the prestretched graft member had been collapsed, during manufacture, by applying heat thereto.

9. The bistable luminal graft endoprosthesis as defined in claim 1 wherein the polymeric material is polycarbonate polyurethane which has a Durometer hardness of 75D or harder.

10. A bistable luminal graft endoprosthesis, comprising:

a stent member having a generally cylindrical external surface and a generally cylindrical internal surface, said stent member being expandable from a first diameter at which it can be inserted into a human or animal body pathway and a second diameter greater than said first diameter; and a polymeric material tubular graft member that engages at least one of said generally cylindrical external and internal surfaces of said stent member, said graft member has a collapsed stable configuration when said stent member is at said first diameter and assumes an expanded stable configuration when said stent member is at said second expanded diameter, said graft member polymeric material having been prestretched to surpass the elastic yield point of the polymeric material, and said collapsed stable configuration of the graft member being one at which the graft member, during manufacture, had been collapsed over at least one of said generally cylindrical surfaces of the stent member to provide said collapsed stable configuration after the graft member polymeric material had been prestretched to surpass the elastic yield point;

said expanded stable configuration of the graft member being one at which the graft member, during use, expands to said second diameter after having been prestretched to surpass said elastic yield point; and said polymeric material is substantially unstressed when at both said collapsed and expanded stable configurations, and said polymeric material is a polycarbonate polyurethane having a Durometer hardness of 75D or harder.

11. The bistable luminal graft endoprosthesis as defined in claim 10 wherein the prestretched graft member had been collapsed, during manufacture, by applying heat thereto.

12. A method for the manufacture of a bistable luminal graft endoprosthesis, comprising the steps of:

supplying a stent member having a generally cylindrical external surface and a generally cylindrical internal surface and capable of being expanded from a first cross-sectional diameter to a second, expanded cross-sectional diameter greater than said first cross-sectional diameter;

preparing a tubular graft member from a polymeric material selected from the group consisting of polyester terephthalate, polytetrafluoroethylene, polyamide, poly(methylpentane), polypropylene, polyethylene, polyvinylchloride, polycarbonate polyurethane which has a Durometer hardness of 75D or harder, and combinations thereof, the tubular graft member having a collapsed stable configuration when the graft member has the first cross-sectional diameter, said tubular graft member has an expanded stable configuration when the graft member has the second, expanded cross-sectional diameter, said preparing step including prestretching the polymeric material of the tubular graft member to surpass the elastic yield point of the polymeric material and achieve said expanded stable configuration;

applying said prestretched tubular graft member to at least one of said generally cylindrical external and internal surfaces of said stent member;

collapsing said prestretched tubular graft member to said collapsed stable configuration over at least one of said cylindrical surfaces of said stent member; and expanding the graft endoprosthesis, when at said collapsed stable configuration, to said second diameter to thereby move the graft member from said collapsed stable configuration to said expanded stable configuration, both said collapsed and expanded stable configurations being substantially unstressed.

13. The method as defined in claim 12 wherein said applying step includes bonding said graft member to said stent member by the use of thermobonding, adhesives, primers, coupling agents or combinations thereof.

14. The method as defined in claim 12 wherein the polymeric material is polycarbonate polyurethane which has a Durometer hardness of 75D or harder.

15. The method as defined in claim 12 wherein said collapsing step includes applying heat to the prestretched tubular graft member.

* * * * *

UNITED STATES PATENT AND TRADEMARK OFFICE
CERTIFICATE OF CORRECTION

PATENT NO. : 5,755,774
DATED : May 26, 1998
INVENTOR(S) : Leonard Pinchuk

It is certified that error appears in the above-identified patent and that said Letters Patent is hereby corrected as shown below:

```
On the Cover Page, under "References Cited, U.S. Patent
    Documents", Patent No. 4,580,568, "Glanturco" should read
    --Gianturco--; under "Other Publications", line 3,
    "Journal -of" should read --Journal of--; in the Abstract,
    line 3, "and as suitable" should read --and is suitable--.
Col. 1, line 38, delete "Approaches" and insert --approaches--;
    line 48, "These prosthesis" should read --These prostheses--;
    line 64, delete the comma after "Tube-formed".
Col. 2, line 7, "rolded axially" should read --folded axially--.
Col. 4, line 48, "worn toward" should read --work toward--.
Col. 5, line 31, delete the comma after "similar to"; lines 46-47,
    "such that" should read --such as that--; line 57,
    "mandrel and, the" should read --mandrel and the--.
Col. 6, line 37, "which Is" should read --which is--.
Col. 7, lines 25-28, delete ", said graft member being constructed
    to surpass said elastic yield point without substantial
    weakening of said graft member when expanded to said second
    diameter".
```

Signed and Sealed this

Second Day of November, 1999

Attest:

Q. TODD DICKINSON

Attesting Officer

Acting Commissioner of Patents and Trademarks